US00PP24822P3

(12) United States Plant Patent

Kitahara et al.

(10) Patent No.: US PP24,822 P3

(45) Date of Patent: Aug. 26, 2014

(54) *GOMPHRENA* PLANT NAMED 'GOM070101'

(50) Latin Name: *Gomphrena hybrida*
Varietal Denomination: GOM070101

(71) Applicants: Akiko Kitahara, Mizuho (JP); Ushio Sakazaki, Shiga (JP)

(72) Inventors: Akiko Kitahara, Mizuho (JP); Ushio Sakazaki, Shiga (JP)

(73) Assignee: Amerinova Properties LLC., Bonsall, CA (US)

( * ) Notice: Subject to any disclaimer, the term of this patent is extended or adjusted under 35 U.S.C. 154(b) by 94 days.

(21) Appl. No.: 13/694,213

(22) Filed: Nov. 7, 2012

(65) Prior Publication Data

US 2014/0130218 P1 May 8, 2014

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

*Primary Examiner* — Kent L Bell

(74) *Attorney, Agent, or Firm* — C. A. Whealy

(57) ABSTRACT

A new and distinct cultivar of *Gomphrena* plant named 'GOM070101', characterized by its mounding plant habit; vigorous growth habit; freely branching habit; large pubescent leaves; and large long-lasting inflorescences with numerous red purple-colored flowers.

1 Drawing Sheet

Botanical designation: *Gomphrena hybrida.*
Cultivar denomination: 'GOM070101'.

BACKGROUND OF THE INVENTION

The present invention relates to a new and distinct cultivar of *Gomphrena* plant, botanically known as *Gomphrena hybrida* and hereinafter referred to by the name 'GOM070101'.

The new *Gomphrena* plant is a product of a planned breeding program conducted by the Inventors in Higashiomi, Shiga, Japan. The objective of the breeding program is to create new mounding *Gomphrena* plants with large long-lasting inflorescences.

The new *Gomphrena* plant was discovered and selected by the Inventors as a single flowering plant from within the progeny of a cross-pollination of an unidentified selection of *Gomphrena macrocephala*, not patented, as the female, or seed, parent with an unidentified selection of *Gomphrena hybrida* as the male, or pollen, parent, in a controlled environment in Higashiomi, Shiga, Japan on Aug. 12, 2006. The new *Gomphrena* plant was discovered and selected by the Inventors as a single flowering plant from within the progeny of the stated cross-pollination in a controlled greenhouse environment in Higashiomi, Shiga, Japan on Jul. 10, 2007.

Asexual reproduction of the new *Gomphrena* plant by terminal cuttings in a controlled environment in Higashiomi, Shiga, Japan since Oct. 5, 2007 has shown that the unique features of this new *Gomphrena* plant are stable and reproduced true to type in successive generations.

SUMMARY OF THE INVENTION

Plants of the new *Gomphrena* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'GOM070101'. These characteristics in combination distinguish 'GOM070101' as a new and distinct *Gomphrena* plant:

1. Mounding plant habit.
2. Vigorous growth habit.
3. Freely branching habit.
4. Large pubescent leaves.
5. Large long-lasting inflorescences with numerous red purple-colored flowers.

Plants of the new *Gomphrena* differ primarily from plants of the female parent selection in the following characteristics:

1. Plants of the new *Gomphrena* are more freely branching than plants of the female parent selection.
2. Plants of the new *Gomphrena* have smaller inflorescences than plants of the female parent selection.

Plants of the new *Gomphrena* differ primarily from plants of the male parent selection in the following characteristics:

1. Plants of the new *Gomphrena* are more mounding than and not as upright as plants of the male parent selection.
2. Plants of the new *Gomphrena* have larger inflorescences than plants of the male parent selection.

Plants of the new *Gomphrena* can be compared to plants of *Gomphrena leontopodioides* 'Balboa', disclosed in U.S. Plant Pat. No. 22,263. In side-by-side comparisons conducted in Higashiomi, Shiga, Japan, plants of the new *Gomphrena* differed primarily from plants of 'Balboa' in the following characteristics:

1. Plants of the new *Gomphrena* had larger leaves than plants of 'Balboa'.
2. Plants of the new *Gomphrena* had larger inflorescences than plants of 'Balboa'.
3. Plants of the new *Gomphrena* and 'Balboa' differed in flower color as plants of 'Balboa' had purple-colored flowers.

BRIEF DESCRIPTION OF THE PHOTOGRAPHS

The accompanying colored photographs illustrate the overall appearance of the new *Gomphrena* plant showing the colors as true as it is reasonably possible to obtain in colored reproductions of this type. Colors in the photographs may differ slightly from the color values cited in the detailed botanical description which accurately describe the colors of the new *Gomphrena* plant.

The photograph at the top of the sheet comprises a side perspective view of a typical flowering plant of 'GOM070101' grown in a container.

The photograph at the bottom of the sheet is a close-up view of a typical flowering plant of 'GOM070101'.

DETAILED BOTANICAL DESCRIPTION

Plants used for the aforementioned photographs and following description were grown under conditions which closely approximate commercial production conditions during the summer in one-gallon containers in a polyethylene-covered greenhouse in Bonsall, Calif. During the production of the plants, day temperatures ranged from 20° C. to 35° C. and night temperatures ranged from 7° C. to 21° C. Plants were pinched one time and were 17 weeks old when the photographs and description were taken. In the following description, color references are made to The Royal Horticultural Society Colour Chart, 2007 Edition, except where general terms of ordinary dictionary significance are used.

Botanical classification: *Gomphrena hybrida* 'GOM070101'.

Parentage:

*Female, or seed, parent.*—Unidentified selection of *Gomphrena macrocephala*, not patented.

*Male, or pollen, parent.*—Unknown selection of *Gomphrena hybrida*, not patented.

Propagation:

*Type.*—By terminal cuttings.

*Time to initiate roots, summer.*—About one to two weeks at 18° C. to 22° C.

*Time to initiate roots, winter.*—About three to four weeks at 18° C. to 22° C.

*Time to produce a rooted young plant, summer.*—About five weeks at 20° C. to 24° C.

*Time to produce a rooted young plant, winter.*—About six weeks at 20° C. to 24° C.

*Root description.*—Fine, fibrous; white in color.

*Rooting habit.*—Moderate branching; moderately dense.

Plant description:

*Plant and growth habit.*—Mounding and open plant habit; globular in overall plant shape; vigorous growth habit.

*Branching habit.*—Freely branching habit; about five to six primary lateral branches develop, each primary lateral branch with secondary lateral branches, pinching enhances secondary lateral branch development.

*Plant height.*—About 21 cm.

*Plant diameter.*—About 34 cm by 36 cm.

Lateral branch description:

*Length.*—About 25 cm.

*Diameter.*—About 5 mm.

*Internode length, vegetative plants.*—About 2.4 cm.

*Internode length, reproductive plants.*—About 4.8 cm.

*Strength.*—Strong.

*Aspect.*—Initially upright and becoming more outwardly spreading with development, secondary laterals about 45° to 60° from primary laterals.

*Texture.*—Densely pubescent, hirsute to lanate.

*Color.*—Close to 146D.

Foliage description:

*Arrangement, vegetative plants.*—Alternate; simple.

*Arrangement, reproductive plants.*—Opposite; subtending the inflorescences, whorled; simple.

*Length.*—About 7.3 cm.

*Width.*—About 3.5 cm.

*Shape.*—Elliptical.

*Apex.*—Acute.

*Base.*—Attenuate.

*Margin.*—Entire; curling upwards.

*Texture, upper surface.*—Pubescent, hirsute or setose; coarse, leathery.

*Texture, lower surface.*—Pubescent, setose; coarse, leathery.

*Texture, margins.*—Pubescent, setose.

*Venation pattern.*—Pinnate with one midvein and arcuate lateral veins.

*Color.*—Developing leaves, upper surface: Close to 146B. Developing leaves, lower surface: Close to 148B. Fully expanded leaves, upper surface: Close to 147A; venation, close to 148C. Fully expanded leaves, lower surface: Close to 148B; venation, close to 146D.

*Petiole length.*—About 6 mm.

*Petiole width, flattened.*—About 5 mm.

*Petiole texture, upper and lower surfaces.*—Pubescent, hirsute.

*Petiole color, upper and lower surfaces.*—Close to 148C.

Flower description:

*Flower arrangement and flowering habit.*—Slender flowers densely arranged in large spherical terminal inflorescences; freely flowering habit with about 186 flowers per inflorescence and about ten to twelve inflorescences developing per plant at a time; single flowers arranged upright and outwardly on cone-shaped receptacles; flowers sessile with a single five-parted perianth and subtended by two slender colored bracts.

*Fragrance.*—None detected.

*Natural flowering season.*—Plants flower from the spring to the fall in Southern California; plants begin flowering about eight weeks after planting.

*Flower longevity.*—Inflorescences last about four weeks on the plant; flowers persistent.

*Inflorescence height.*—About 3.5 cm.

*Inflorescence diameter.*—About 4 cm.

*Flower height.*—About 2.6 cm.

*Flower diameter.*—About 3 mm by 5 mm.

*Flower buds.*—Length: About 2.4 cm. Diameter: About 5 mm. Shape: Narrow, elongated. Color: Close to 72D.

*Perianth segments.*—Quantity and arrangement: Five segments in a single flattened whorl. Shape: Lanceolate. Apex: Acute. Base: Truncate; surrounded by white-colored hairs. Margin: Entire. Length: About 2.2 cm. Width: About 2 mm. Texture, upper and lower surfaces: Smooth, glabrous; papery. Color: When opening, upper and lower surfaces: Close to N74D.

Fully opened, upper surface: Close to 72C. Fully opened, lower surface: Close to 70B.

*Sepals.*—Sepal development has not been observed on plants of the new *Gomphrena.*

*Bracts.*—Quantity and arrangement: Two, subtending each individual flower. Length: About 2.8 cm to 3 cm. Width, at the base: About 5 mm. Shape: Lanceolate. Apex: Acute. Base: Attenuate. Texture, upper and lower surfaces: Smooth, glabrous; papery. Color: When opening, upper and lower surfaces: Close to 70B. Fully opened, upper and lower surfaces: Towards the apex, close to 70B; towards the base, close to 76C.

*Peduncles.*—Length: About 4 cm. Diameter: About 6 mm. Strength: Strong. Texture: Densely pubescent; hirsute. Color: Close to 145A.

*Reproductive organs.*—Stamens: Quantity and arrangement: Five per flower; filaments united in a cylindrical tube encasing the gynoecium. Filament length: About 2.2 cm. Filament color: Towards the apex, close to N74D; towards the base, close to 76C. Anther shape: Oblong. Anther length: About 1.5 mm. Anther color: Close to 161C. Pollen amount: Scarce. Pollen color: Close to 9A.

*Pistils.*—Quantity: One per flower. Pistil length: About 6 mm. Style length: About 1 mm. Style color: Close to 145D. Stigma shape: Bi-parted. Stigma color: Close to 145D. Ovary color: Close to 145B.

*Seeds and fruits.*—Seed and fruit development have not been observed on plants of the new *Gomphrena.*

Pathogen & pest resistance: Plants of the new *Gomphrena* have not been observed to be resistant to pests and pathogens common to *Gomphrena* plants.

Garden performance: Plants of the new *Gomphrena* have been observed to have good garden performance and to tolerate wind, rain and temperatures ranging from about 1° C. to 35° C.

It is claimed:

1. A new and distinct *Gomphrena* plant named 'GOM070101' as illustrated and described.

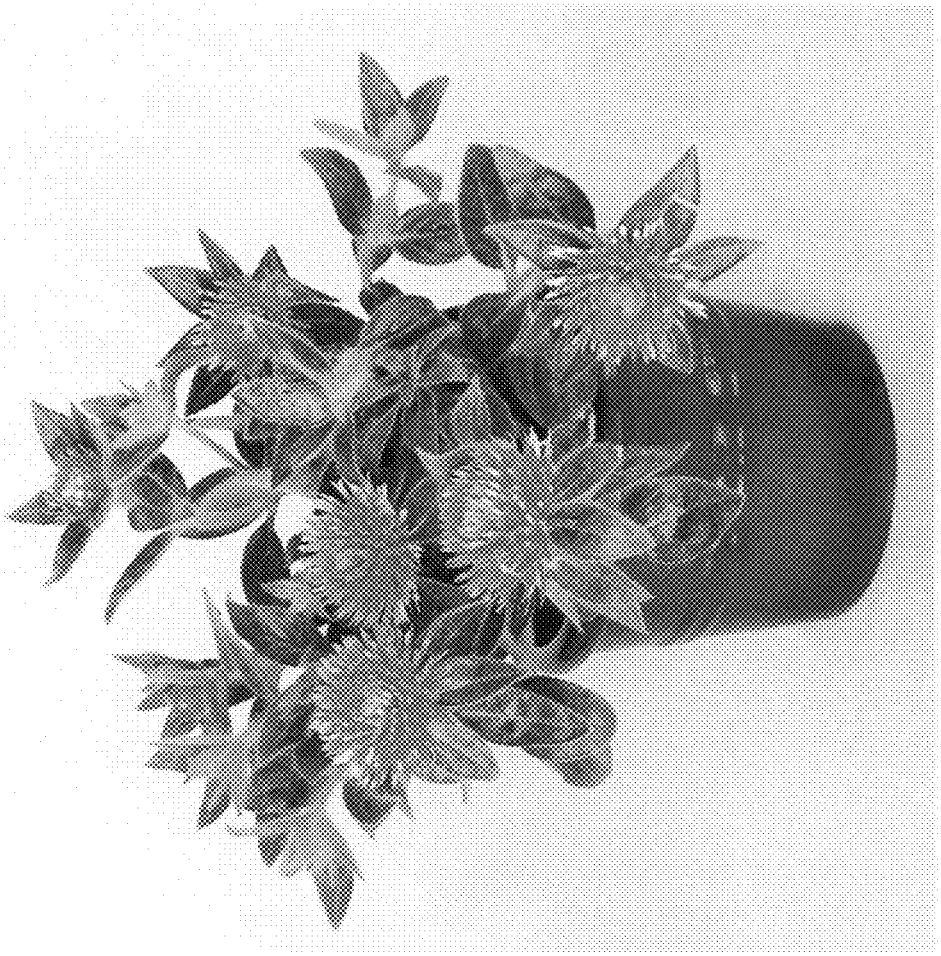
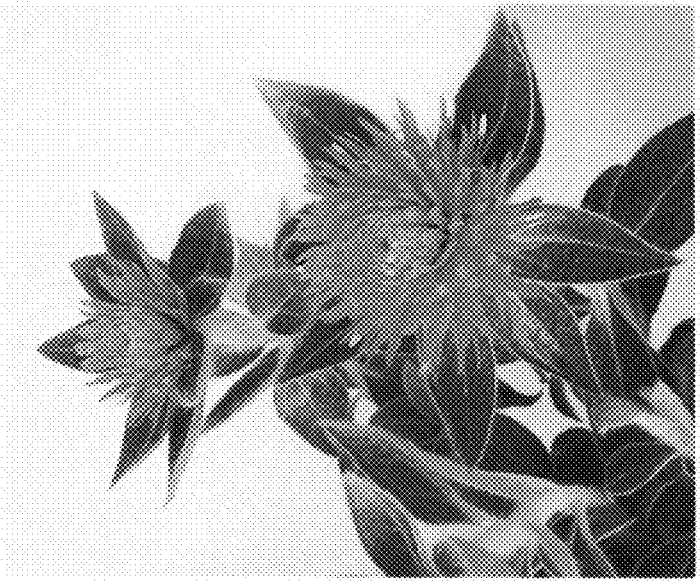

* * * * *